United States Patent
Lei

(10) Patent No.: US 9,347,082 B2
(45) Date of Patent: May 24, 2016

(54) AUTOMATED CELL GROWTH/MIGRATION DETECTION SYSTEM AND ASSOCIATED METHODS

(71) Applicant: OmniVision Technologies, Inc., Santa Clara, CA (US)

(72) Inventor: Junzhao Lei, San Jose, CA (US)

(73) Assignee: OmniVision Technologies, Inc., Santa Clara, CA (US)

(*) Notice: Subject to any disclaimer, the term of this patent is extended or adjusted under 35 U.S.C. 154(b) by 20 days.

(21) Appl. No.: 14/471,890

(22) Filed: Aug. 28, 2014

(65) Prior Publication Data
US 2016/0060676 A1  Mar. 3, 2016

(51) Int. Cl.
*G06K 9/00* (2006.01)
*C12Q 1/02* (2006.01)

(52) U.S. Cl.
CPC .......................................... *C12Q 1/02* (2013.01)

(58) Field of Classification Search
USPC .......................................................... 382/133
See application file for complete search history.

(56) References Cited

U.S. PATENT DOCUMENTS 8,922,662 B1 * 12/2014 Fu .................. H04N 5/23264
348/208.12
2013/0194410 A1 * 8/2013 Topman .............. G06K 9/0014
348/79
2014/0050386 A1 * 2/2014 Humayun .............. A61L 27/38
382/133
2014/0205176 A1 * 7/2014 Obrien .................. G02B 21/365
382/134

OTHER PUBLICATIONS

Gehler et al., A novel automatable cell migration assay for high content screening, 2010, platypus technologies poster, http://www.platypustech.com/posters/SBS_April2010_OrisPro_lowres.pdf.*

* cited by examiner

*Primary Examiner* — John Strege
(74) *Attorney, Agent, or Firm* — Lathrop & Gage LLP

(57) ABSTRACT

An automated cell growth/migration detection system includes: a container for containing a cell growth/migration matrix/medium into which deposited cells form a cell surface; an image sensor for capturing images; an actuator for incrementally varying distance between the image sensor lens and the cell surface such that the images correspond to varying imaging depths; and an image data processor for processing the images to determine cell growth/migration. An automated cell growth/migration detection method includes: capturing a first image series of a cell surface within a first imaging cycle corresponding to a sequence of imaging depths between the cell surface and an image sensor; capturing an additional image series of the cell surface within each of at least one additional imaging cycle and corresponding to the same sequence of imaging depths; processing each image series for each imaging cycle to determine a clearest-looking image; and determining cell growth/migration from the clearest-looking image.

21 Claims, 6 Drawing Sheets

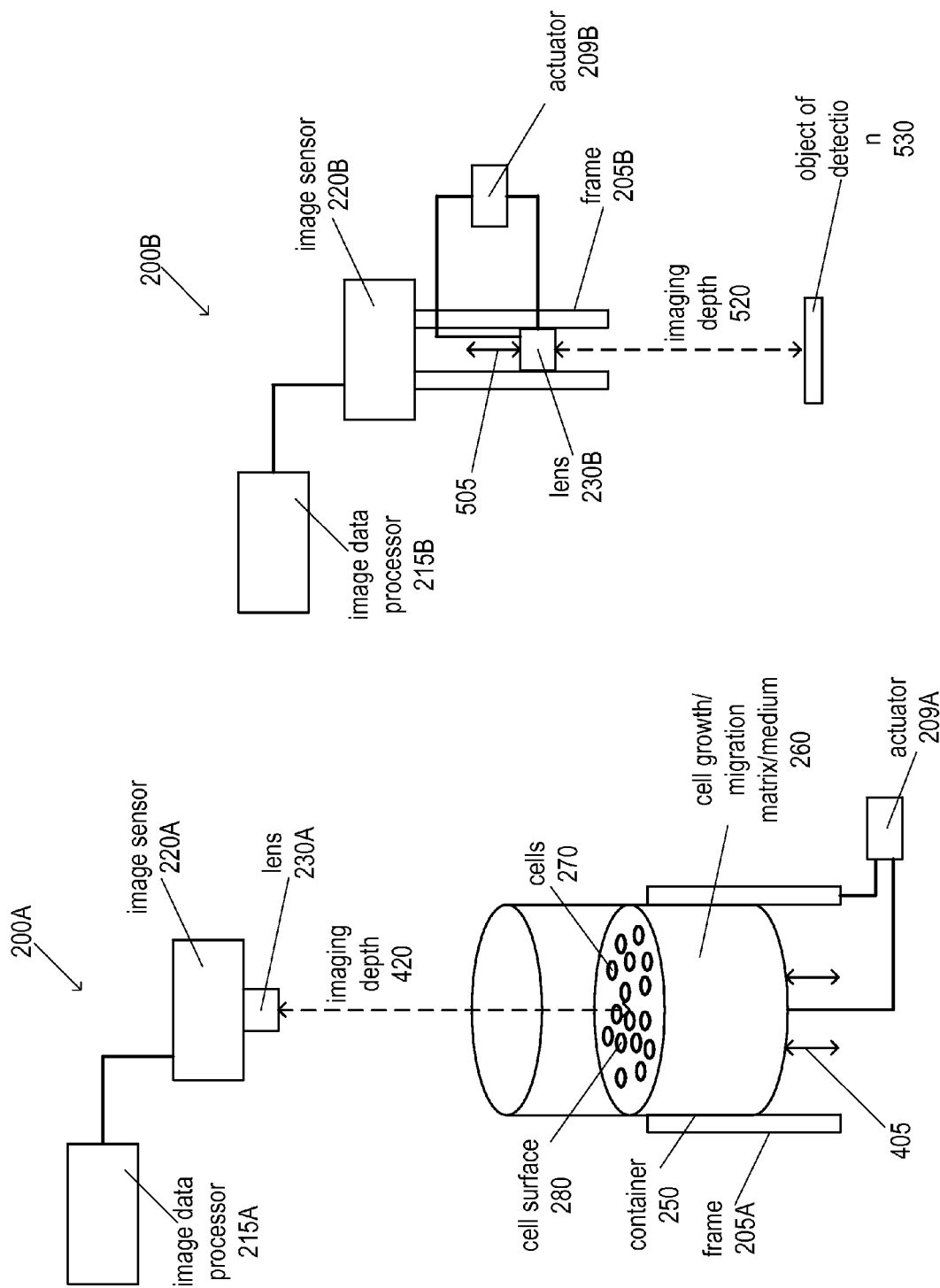

AUTOMATED CELL GROWTH/MIGRATION DETECTION SYSTEM AND ASSOCIATED METHODS

BACKGROUND INFORMATION

Cell growth assays, alternatively known as cell proliferation assays, are useful in medical diagnostic technology, as are cell migration assays. However, these assays are routinely done manually. First, the cells are deposited on a growth matrix or medium. Then a cell growth/migration stimulus, e.g., a growth factor, is added and the cells are allowed to proliferate and/or migrate. The course of cell growth/migration is tracked manually by a human operator observing the cells under a microscope periodically over many hours, e.g., sixteen hours. This manual tracking process is labor intensive, and raises the cost of these assays.

SUMMARY

In an embodiment, an automated cell growth/migration detection system includes: a container for containing a cell growth/migration matrix/medium into which deposited cells form a cell surface; an image sensor having a lens and capturing images through the lens; an actuator for incrementally varying distance between the lens and the cell surface such that the images correspond to varying imaging depths; and an image data processor for processing the images to determine cell growth/migration.

In an embodiment, an automated cell growth/migration detection method includes: setting a first imaging depth between a cell surface and an image sensor; capturing, with the image sensor, a first image of the cell surface; setting a second imaging depth between the cell surface and the image sensor; capturing, with the image sensor, a second image of the cell surface; and processing the first and second images to determine cell growth/migration.

In an embodiment, an automated cell growth/migration detection method includes: capturing a first series of images of a cell surface within a first imaging cycle corresponding to a sequence of imaging depths between the cell surface and an image sensor; capturing an additional series of images of the cell surface within each of at least one additional imaging cycle and corresponding to the same sequence of imaging depths between the cell surface and an image sensor; processing each series of images for each imaging cycle to determine a clearest-looking image; and from the clearest-looking image of each imaging cycle, determining cell growth/migration.

BRIEF DESCRIPTION OF THE SEVERAL VIEWS OF THE DRAWINGS

FIG. 4 a schematic diagram illustrating another embodiment of an automated cell growth/migration detection system.

FIG. 5 a schematic diagram illustrating yet another embodiment of an automated cell growth/migration detection system.

DETAILED DESCRIPTION

Embodiments disclosed below detect cell growth and migration (herein denoted as growth/migration). Particular embodiments relate to optical systems that detect cell growth/migration; these systems utilize image sensors with adjustable imaging depths and may automatically vary the imaging depths to periodically obtain cell growth/migration images.

Figure 1B:
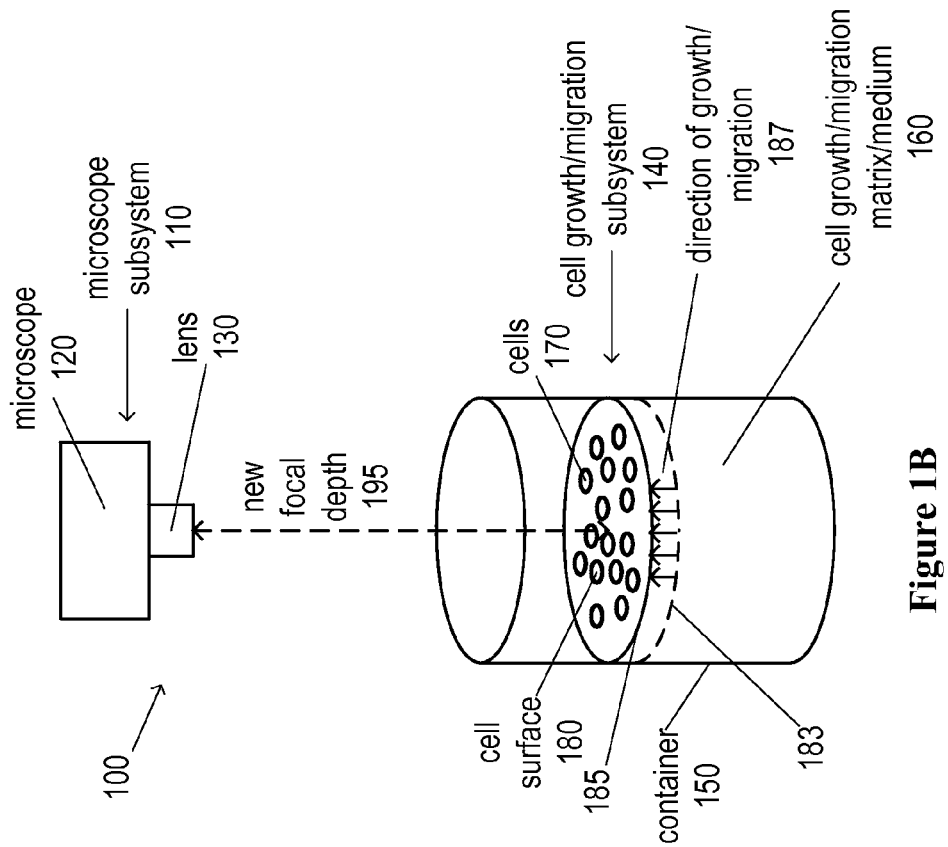
FIG. 1B is a schematic diagram of a manually based cell growth/migration detection system after a period of cell growth/migration.
Figure 1A:
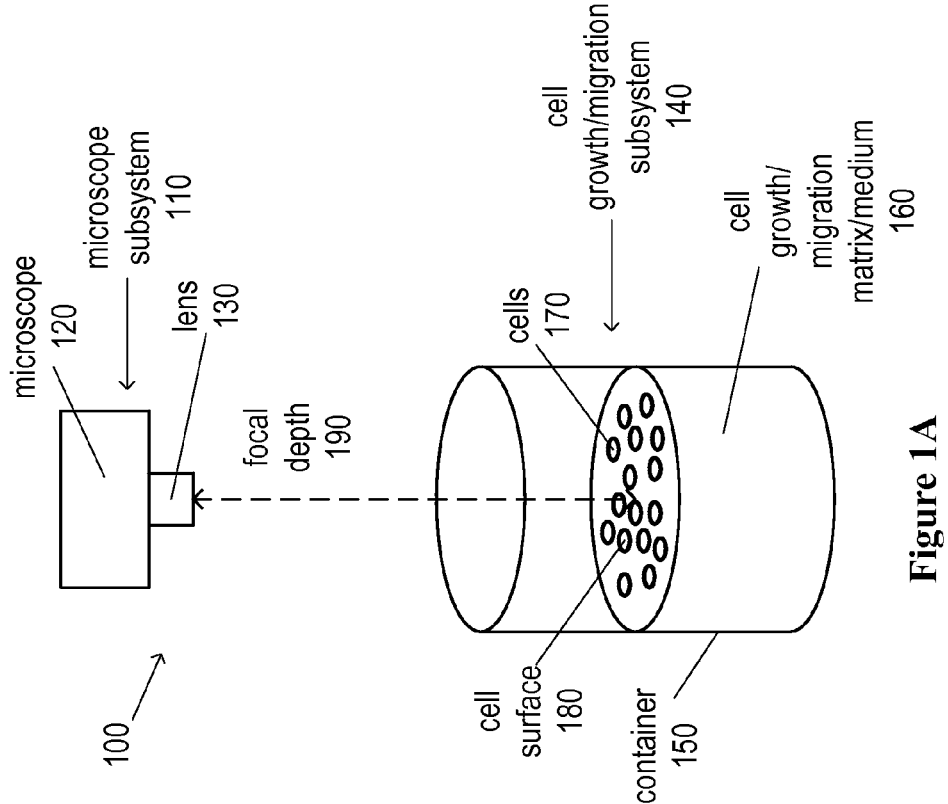
FIG. 1A is a schematic diagram of a manually based cell growth/migration detection system.

FIG. 1A is a schematic diagram illustrating a manually based cell growth/migration detection system 100. This system 100 includes a microscope subsystem 110, which further includes a microscope 120 with its lens or lens system 130. Also included in system 100 is a cell growth/migration subsystem 140, which further includes a container 150 that holds cell growth/migration matrix/medium 160, which may include cell growth/migration stimulant factors, e.g., growth factors. Cells 170 are deposited on top of the matrix/medium 160. Alternatively, cells 170 may be deposited inside the matrix/medium 160. Cells 170 may be deposited to form a layer, a clump, or other types of formations. Cell surface 180 of the cells 170 is the object of detection. The microscope subsystem 110 is adjusted manually by an operator to obtain a first clear visual image of the top of cell surface 180, as determined by the operator. Focal depth 190 is the resultant distance between lens 130 and cell surface 180. Alternatively, other surfaces of the cells 170 may be the object of detection, depending on the relative positions of the microscope subsystem 110 and the cell growth/migration subsystem 140. For example, if the microscope subsystem 110 is situated below the cell growth/migration subsystem 140, then the bottom surface (not shown) of the cells 170 will be object of detection.

FIG. 1B is a schematic diagram illustrating the cell growth/migration detection system 100 after a period of cell growth/migration. Specifically as the cells 170 grow and proliferate, the cell surface 180 gradually moves in an upward direction, as shown by arrows 187, from its initial position 183 (corresponding to where cell surface 180 was in FIG. 1A) to a new position 185. Accordingly, after manually obtaining a second clear visual image of the cell surface 180 in FIG. 1B, the resultant new focal depth 195 may be different from the previous focal depth 190. For example, the new focal depth 195 may become shorter than the previous focal depth 190. By keeping track of the focal depth and plotting it against time, a quantitative cell growth assessment may be obtained.

Alternatively, cells 170 may be initially deposited inside the matrix/medium 160. Stimulus, such as chemical and/or biological stimulus, may be applied to the cells 170 and/or the matrix/medium 160 to cause cell surface 180 to migrate over time. In certain cell migration assays, the cell surface 180 may migrate downwards, away from the microscope subsystem 110. The operator manually adjusts the focal depth 190 to obtain a clear image of the cell surface 180, and repeats the process over time. Quantitative cell migration assessment may be obtained by plotting positional information of the cell surface 180, e.g., focal depth, against time.

Figure 2:
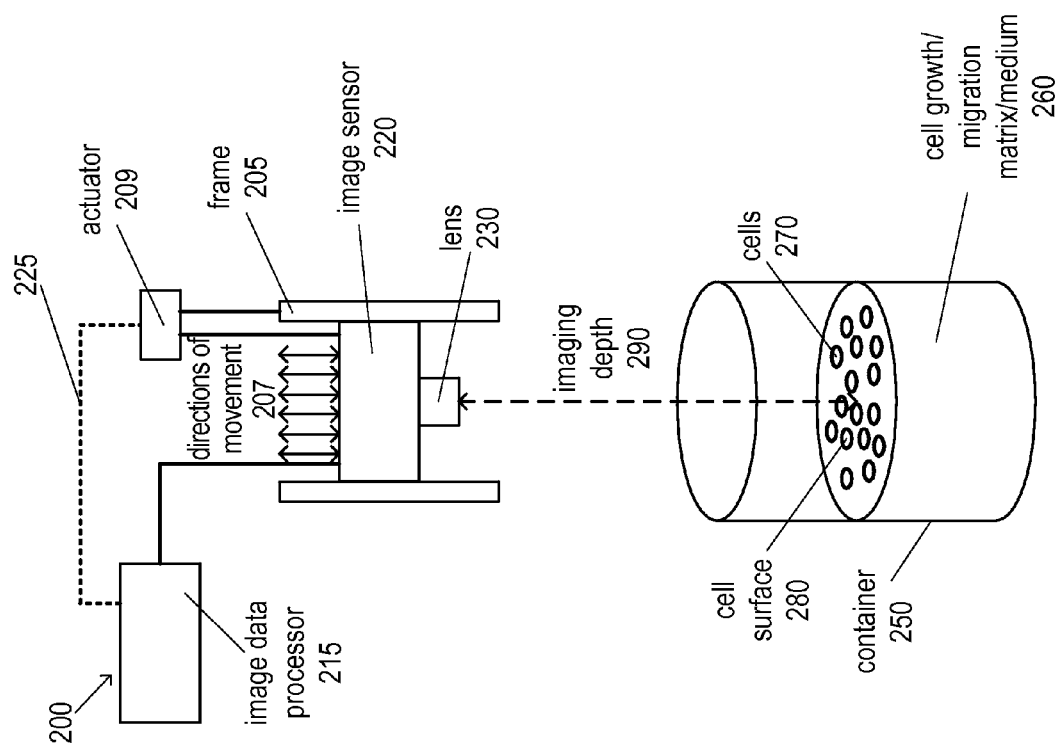
FIG. 2 is a schematic diagram illustrating an embodiment of an automated cell growth/migration detection system.

FIG. 2 is a schematic diagram illustrating an embodiment of an automated cell growth/migration detection system 200, which detects cell growth/migration by varying imaging depths and obtaining cell growth or migration images periodically. This automated cell growth/migration detection system 200 includes an image sensor 220 with a lens 230 to obtain image data, as well as an image data processor 215 coupled to image sensor 220 to process the image data. The image sensor 220 may be a CMOS image sensor, a CCD image sensor, or another type of image sensors. In the present embodiment, image sensor 220 is mechanically coupled to a frame 205 such that it is capable of moving up and down within the frame 205, as depicted by arrows 207. A non-human actuator 209 (e.g., a linear actuator) is electrically, mechanically, or otherwise coupled to either the image sensor 220, or the frame 205, or both, in order to actuate relative movement between the image sensor 220 and the frame 205. In the present embodiment, the actuator 209 causes the relative movement by moving the image sensor 220. In an embodiment image data processor 215 also sends commands to actuator 209 via control line 225 to control the relative movement depicted by arrows 207 (however those skilled in the art should appreciate that control of actuator 209 may exist elsewhere without departing from the scope hereof, including or example within image sensor 220 or actuator 209); the commands may include incremental movements of actuator 209 through a fixed range of distance, as described below, or may depend upon detected image quality. Also included in the automated system 200 is a container 250 that holds cell growth/migration matrix/medium 260, which may include cell growth/migration stimulant factors, e.g., growth factors. Cells 270 are deposited on top of the matrix/medium 260. Alternatively, cells 270 may be deposited inside the matrix/medium 260. Cell surface 280 of the cells 270 is the object of detection.

Figure 3B:
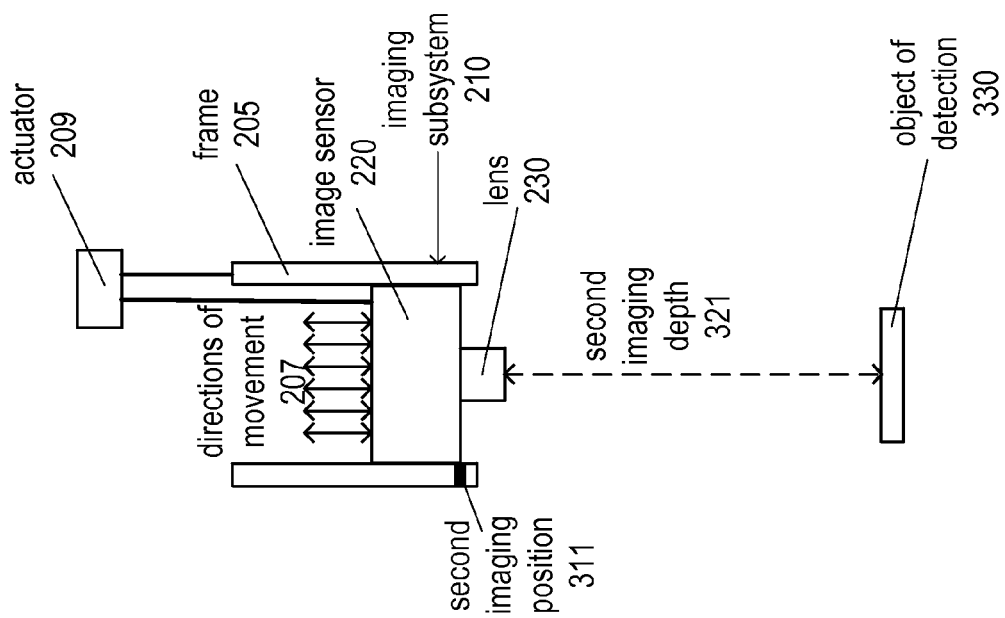
FIG. 3B shows an embodiment of an automated cell growth/migration detection system wherein a second image is taken with a second imaging depth, sometime after the first image has been taken.
Figure 3A:
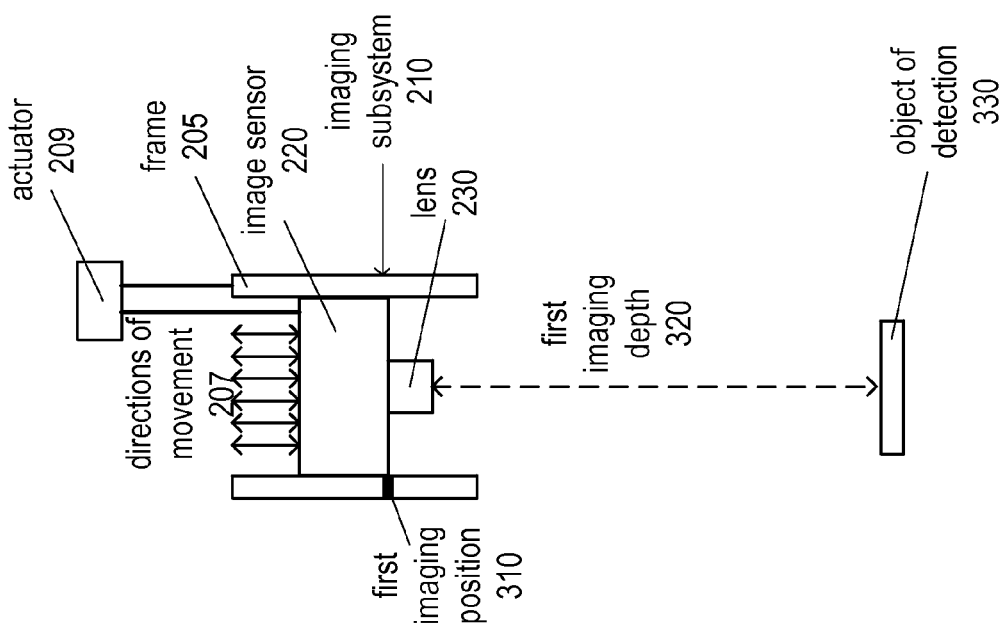
FIG. 3A shows an embodiment of an automated cell growth/migration detection system wherein a first image is taken with a first imaging depth.

The operation to detect the cell surface 280 is automated as shown in FIGS. 3A and 3B. First, the image sensor 220 is moved to a first imaging position 310 along the frame 205 by the actuator 209, as shown in FIG. 3A. A first imaging depth 320 is the resultant distance between the lens 230 and an object of detection 330. The object of detection 330 may be the top of cell surface 280 as shown in FIG. 2. After being moved to the first imaging position 310, the image sensor 220 takes a first image of the object of detection 330. This first image may or may not be in focus, as there is no human operator to adjust the position of image sensor 220 to obtain a clear image. The resulting image data is sent to image data processor 215 (not shown in FIGS. 3A, 3B) coupled to the image sensor 220. After taking the first image, the image sensor 220 is moved to a second imaging position 311 along the frame 205 by the actuator 209, as shown in FIG. 3B. A second imaging depth 321 is the resultant distance between the lens 230 and the object of detection 330. After being moved to the second imaging position 311, the image sensor 220 takes a second image of the object of detection 330, and sends the resulting image data to the image data processor 215. The second image may or may not be in focus, as there is no human operator to adjust the position of image sensor 220 to obtain a clear image. The first imaging depth 320 may be longer than the second imaging depth 321, or shorter, depending on whether the image sensor 220 is being moved down or up.

Incremental imaging depth, i.e., the difference between the first imaging depth 320 and the second imaging depth 321 may be predetermined to be about 0.1 µm to 10 µm, e.g., 1 µm. One way to set the incremental imaging depth is to consider (from prior knowledge, e.g., prior observations, or scientific literature) the entire range of the growth/migration of the cell surface 280, and subdivide this range by a predetermined divisor number. The resulting division is taken as the incremental imaging depth. For example, in a cell growth assay, based on prior observations, the cell surface 280 may move upward for about 7 µm during the course of the assay. Selecting the divisor number to be seven and dividing 7 µm by seven yields an incremental imaging depth of 1 µm. Alternatively, dividing 7 µm by fourteen yields an incremental imaging depth of 0.5 µm. The image sensor 220 may thus be moved further down or up along frame 205 to a third imaging position (not shown) to take a third image, then a fourth imaging position (not shown) to take a fourth image, and so on. For example, the image sensor 220 may be moved in increments of 1 µm for a total of eight imaging positions to cover an entire range of 7 µm. Alternatively, the image sensor 220 may be moved in increments of 0.5 µm for a total of fifteen imaging positions to cover an entire range of 7 µm. After taking the final image at the completion of a first imaging cycle, the image sensor 220 is returned to its starting position, i.e., the first imaging depth 320. This completes the full first imaging cycle, and a second imaging cycle may commence. Subsequent imaging cycles may be similarly executed. The time duration of an imaging cycle may be similarly predetermined as previously disclosed. For example, the time duration of an imaging cycle may be set between about $1.5\text{-}15\times10^3$ seconds, e.g., fifteen seconds. The number of imaging cycles may be on the order of magnitude of about 10 to $10^4$, e.g., $10^2$.

In embodiments, the incremental imaging depths, entire range and imaging cycles just described may be programmed into actuator 209 or image data processor 215 (e.g., set via control line 225, FIG. 2). The design parameters disclosed above, including the difference between two imaging depths, direction of moving the image sensor along the frame, the time duration of an imaging cycle, the number of imaging positions per imaging cycle, the number of imaging cycles, etc., are only illustrative and not limiting; other parameters may be used without departing from the scope hereof.

In the disclosure above, the imaging depths between the image sensor 220 and the object of detection 330 are adjusted by the actuator 209 by moving the image sensor 220 along the frame 205, as shown in FIGS. 2, 3A and 3B. In an alternative embodiment, shown in FIG. 4 as automated cell growth/migration detection system 200A, test container 250 is moved up or down (as indicated by the arrows 405) along frame 205A by actuator 209A. As a result, imaging depth 420 (between lens 230 and the cell surface 280 as the object of detection) may be varied. In another alternative embodiment, shown in FIG. 5 as automated cell growth/migration detection system 200B, lens 230B is moved up or down (as indicated by the arrow 505) along frame 205B by actuator 209B. As a result, imaging depth 520 between lens 230B and object of detection 530 is varied (and so is the distance between the image sensor 220B and the lens 230B). In FIG. 5, these two factors (image depth 520 and the distance between image sensor 220B and lens 230B) combine to determine whether the image taken of the object of detection 530 will be in focus or out of focus.

Figure 6:
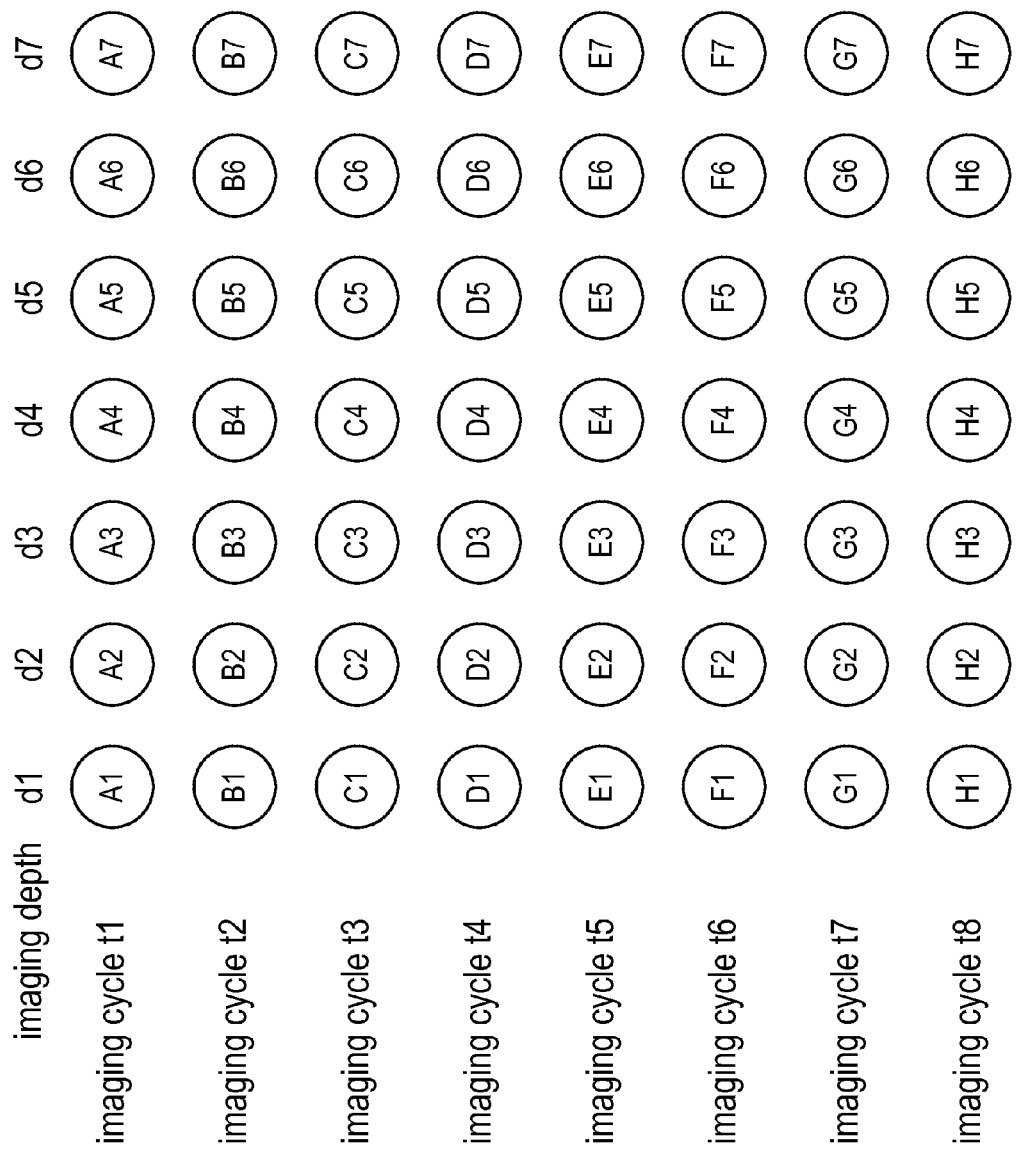
FIG. 6 illustrates example images collected by an automated cell growth/migration detection system over a number of imaging cycles during an automated cell growth/migration assay, in an embodiment.

In an embodiment, image data processor 215, 215A, 215B analyzes the image data collected over the imaging cycles by using an algorithm to determine a best focal depth for each imaging cycle. FIG. 6 is an illustrative example of images collected over a number of imaging cycles during an automated cell growth/migration assay. The images are arranged in a matrix formation, wherein the rows indicate cycles of imaging (t1, t2, etc.), which is time information t, and the columns indicate imaging depths (d1, d2, etc.), which is position information d. In this two dimensional-image matrix, image A1 is the image taken at imaging depth d1 during the first imaging cycle t1; image A2 is the image taken at imaging depth d2 during the first imaging cycle t1; image B1 is the image taken at imaging depth d1 during the second imaging cycle t2; image B2 is the image taken at imaging depth d2 during the second imaging cycle t2; and so on. A machine algorithm, such as one executed by a computer (or by image data processor 215, 215A, 215B), analyzes the first row of images A1, A2, etc., and determines the clearest-looking image. There are several ways to analyze and determine a clearest-looking image. In one example, the algorithm identifies and examines the boundaries of a cell object, and determines how wide they are; the image with the thinnest boundaries is deemed the clearest-looking image. The analysis to determine the clearest-looking image is performed for every row of images (i.e., imaging cycle t1, imaging cycle t2, etc.). As a result, for each of the imaging cycle, t1, t2, etc., a clearest-looking image is identified. The imaging depth associated with the clearest-looking image is deemed as the most focused imaging depth of that imaging cycle. For example, in cycle t1, the most focused imaging depth may be determined to be d1. This generates an ordered pair (t1, d1), which is indicative of the position of the cell surface 280 during the imaging cycle t1. Other ordered pairs are similarly generated, for example, (t2, d1), (t3, d3), (t4, d6), (t5, d6), (t6, d7), (t7, d7), (t8, d7) and so on.

Figure 7A:
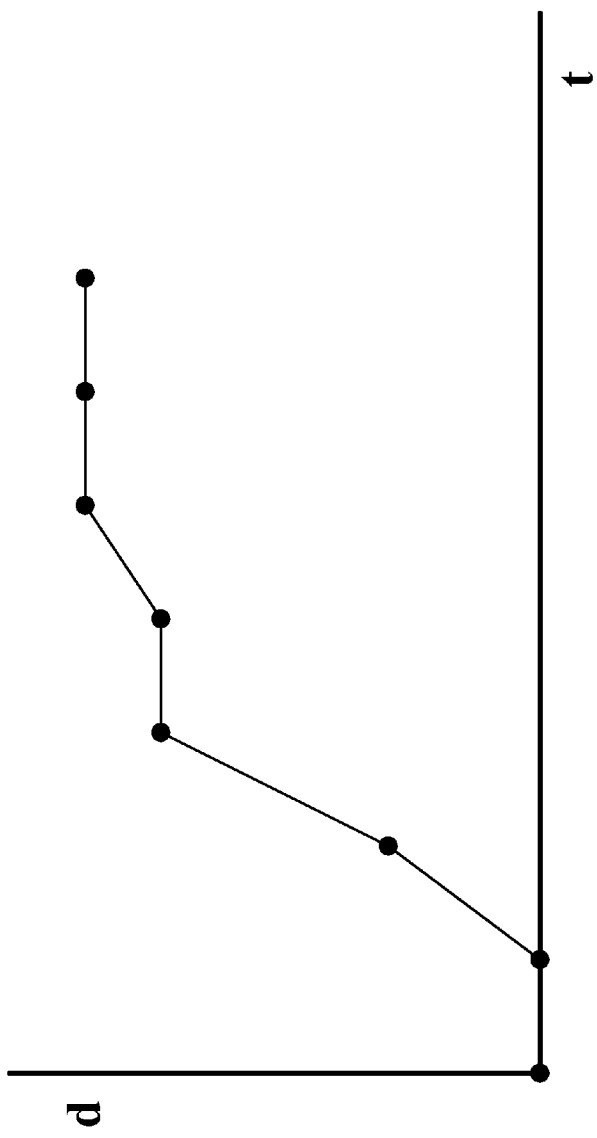
FIG. 7A is an illustrative example of cell growth/migration profile plot.
Figure 7B:
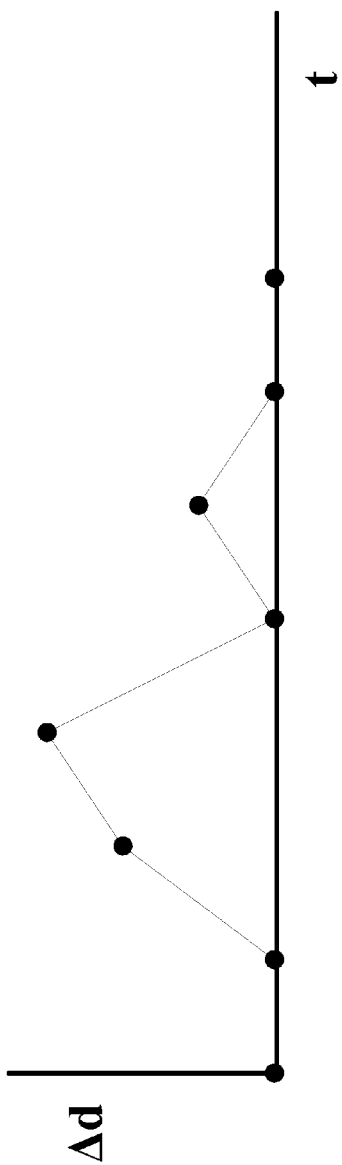
FIG. 7B is another illustrative example of cell growth/migration profile plot.

These ordered pairs, as well as their variations, may then be plotted to give a profile of cell growth/migration over time, as shown in FIGS. 7A and 7B. For illustrative purpose, the vertical axis conveys positional information (d or Δd) of each imaging cycle, whereas the horizontal axis conveys time information (t). In FIG. 7A, each d value is subtracted from the first d value d1 to obtain a value that is directly indicative of the position of the cell surface 280. This generates a new set of ordered pairs as (t1, 0), (t2, 0), (t3, d1-d3), (t4, d1-d6), (t5, d1-d6), (t6, d1-d7), (t7, d1-d7), (t8, d1-d7), which are then plotted in FIG. 7A. Alternative plots may be used to give the cell growth/migration profile. For example, the change in imaging depths, e.g., Δd=d2−d1=d3−d2, etc., may be used to represent the rate of change in position of the cell surface 280 during cell growth/migration, and plotted against time cycles t, as shown in FIG. 7B.

The automated cell growth/migration detection system disclosed above obviates the need of a human operator to obtain a focal depth by manually adjusting imaging depth over the course of cell growth/migration. This provides significant labor saving and reduces the cost of cell growth/migration assays.

In the description above, specific details have been set forth in order to provide understanding of embodiments. However, other embodiments may be practiced without some of these specific details. The scope of the invention is not to be determined by the specific examples provided above but by the claims below. Equivalent relationships to those illustrated in the drawings and described in the specification are encompassed within embodiments. In certain instances, well-known systems, structures, devices, and operations have been shown in block diagram form or without detail in order to avoid obscuring the understanding of the description. Also, the above description of illustrated embodiments of the invention, including what is described in the Abstract, is not intended to be exhaustive or to limit the invention to the precise forms disclosed. While specific embodiments of, and examples for, the invention are described for illustrative purposes, various modifications are possible within the scope of the invention, as those skilled in the relevant art will recognize.

Certain methods disclosed herein have been shown and described in a basic form, although operations may optionally be added to and/or removed from the methods. In addition, a particular order of the operations may have been shown and/or described, although alternate embodiments may perform certain operations in different order, combine certain operations, overlap certain operations, etc.

Thus changes may be made in the above description without departing from the scope hereof, and the above description or accompanying drawings should be interpreted as illustrative and not limiting. The invention includes all modifications and equivalents of the subject matter recited in the claims appended hereto as permitted by applicable law; and combination of the above-described elements in all possible variations thereof is encompassed thereby unless otherwise indicated herein or otherwise clearly contradicted by context.

Combinations of Features

Features described above as well as those claimed below may be combined in various ways without departing from the scope hereof. For example, it will be appreciated that aspects of an automated cell growth/migration detection system described herein may incorporate or swap features of another automated cell growth/migration detection system described herein. The following examples illustrate possible, non-limiting combinations of embodiments described above. It should be clear that many other changes and modifications may be made to the methods and device herein without departing from the spirit and scope of this invention:

(A1) An automated cell growth/migration detection system may include a container for containing a cell growth/migration matrix/medium into which deposited cells form a cell surface; an image sensor having a lens and capturing images through the lens; an actuator for incrementally varying distance between the lens and the cell surface such that the images correspond to varying imaging depths; and an image data processor for processing the images to determine cell growth/migration.

(A2) In the automated cell growth/migration detection system denoted as (A1), the actuator may vary distance at least once so that at least two images are captured by the image sensor, each one of the two images corresponding to a different imaging depth.

(A3) Either of the automated cell growth/migration detection systems denoted as (A1) or (A2) may further include a frame coupled with one or all of the image sensor, lens and container, wherein (a) the actuator translates the image sensor, relative to the frame, to vary the distance, (b) the actuator translates the container, relative to the frame, to vary the distance, and/or the actuator translates a lens, relative to the frame, to vary the distance and vary separation between the lens and the image sensor.

(A4) In any of the automated cell growth/migration detection systems denoted as (A1) through (A3), at a first imaging depth the image sensor may obtain a first image of the cell surface to be stored in the image data processor. At a second imaging depth the image sensor may obtain a second image of the cell surface to be stored in the image data processor. The first and second images comprise a first imaging cycle.

(A5) In any of the automated cell growth/migration detection systems denoted as (A4), after the first imaging cycle and at a third imaging depth, the image sensor may obtain a third image of the cell surface to be stored in the image data processor. After the first imaging cycle and at a fourth imaging depth, the image sensor may obtain a fourth image of the cell surface to be stored in the image data processor. The third and fourth images comprise a second imaging cycle. The third and fourth imaging depths may be the same or different from the first and second imaging depths.

(A6) In any of the automated cell growth/migration detection systems denoted as (A5), the actuator may further vary the distance between the lens and the cell surface to set additional imaging depths between the lens and the cell surface as part of the first imaging cycle.

(A7) In any of the automated cell growth/migration detection systems denoted as (A6), after the first imaging cycle, the actuator may reset the distance between the lens and the cell surface to match the first imaging depth. At the first imaging depth the image sensor obtains a first additional image of the cell surface to be stored in the image data processor.

(A8) In any of the automated cell growth/migration detection systems denoted as (A7), the actuator may reset the distance between the lens and the cell surface to match the second imaging depth. At the second imaging depth the image sensor may obtain a second additional image of the cell surface to be stored in the image data processor.

(A9) In any of the automated cell growth/migration detection systems denoted as (A8), the first additional image and the second additional image may be used by the image data processor to comprise the second imaging cycle.

(A10) In any of the automated cell growth/migration detection systems denoted as (A9), the actuator may further reset the distance between the lens and the cell surface to create further additional imaging depths. Each of the further additional imaging depths may match each of the additional imaging depths of the first imaging cycle at which the image sensor obtains further additional images of the cell surface. Each of the further additional images may be obtained at each of the further additional imaging depths. The further additional images may be used by the image data processor to comprise the second imaging cycle.

(A11) In any of the automated cell growth/migration detection systems denoted as (A10), the image sensor and the actuator may create further imaging cycles.

(A12) In any of the automated cell growth/migration detection systems denoted as (A11), the image data processor may determine a clearest-looking image for each imaging cycle.

(A13) In any of the automated cell growth/migration detection systems denoted as (A1) through (A12), a first set of images may correspond to a first imaging cycle and a second set of images may correspond to a second imaging cycle later than the first imaging cycle. The image data processor may process images from the first imaging cycle to isolate a first clearest-looking image corresponding to a first imaging depth. The image data processor may process images from the second imaging cycle to isolate a second clearest-looking image corresponding to a second imaging depth, wherein difference between the first and second imaging depths determines the cell growth/migration.

(A14) In any of the automated cell growth/migration detection systems denoted as (A1) through (A13), sequential sets of images may correspond to sequential imaging cycles through incremental imaging depths over the distance to form a two-dimensional image matrix processable to determine the cell growth/migration.

(A15) In any of the automated cell growth/migration detection systems denoted as (A14), the image processor, or a computer connected with the image processor, may algorithmically process the two-dimensional image matrix to determine the cell growth/migration.

(A16) In any of the automated cell growth/migration detection systems denoted as (A15), the algorithmic processing may include utilizing cell object boundaries in the two-dimensional image matrix.

(A17) In any of the automated cell growth/migration detection systems denoted as (A1) through (A16), the image data processor may control the actuator to incrementally vary the distance between the lens and the cell surface.

(A18) In any of the automated cell growth/migration detection systems denoted as (A17), the image data processor may control the actuator such that, at the distance, the image sensor focuses on the cell surface.

(A19) In any of the automated cell growth/migration detection systems denoted as (A1) through (A18), the actuator may set the distance by (a) moving the image sensor along a frame, (b) moving the container along the frame, and/or (b) moving the lens along the frame.

(A20) An automated cell growth/migration detection method may include: (1) setting a first imaging depth between a cell surface and an image sensor; capturing, with the image sensor, a first image of the cell surface; (2) setting a second imaging depth between the cell surface and the image sensor; capturing, with the image sensor, a second image of the cell surface; and (3) processing the first and second images to determine cell growth/migration.

(A21) In the automated cell growth/migration detection method denoted as (A20), the cell surface being formed of deposited cells within a cell growth/migration matrix/medium held by a container, the steps of setting may include utilizing an actuator to vary distance between (a) the cell surface and (b) the image sensor or a lens of the image sensor.

(A22) An automated cell growth/migration detection method may include: (1) capturing a first series of images of a cell surface within a first imaging cycle corresponding to a sequence of imaging depths between the cell surface and an image sensor; (2) capturing an additional series of images of the cell surface within each of at least one additional imaging cycle and corresponding to the same sequence of imaging depths between the cell surface and an image sensor; and (3) processing each series of images for each imaging cycle to determine a clearest-looking image; and from the clearest-looking image of each imaging cycle, determining cell growth/migration.

(A23) In the automated cell growth/migration detection method denoted as (A22), the cell surface being formed of deposited cells within a cell growth/migration matrix/medium held by a container, the steps of capturing may include varying the imaging depths by (a) moving the image sensor, (b) moving the container, and/or (b) by moving a lens of the image sensor.

What is claimed is:

1. Automated cell growth/migration detection system, comprising:
   a container for containing a cell growth/migration matrix/medium into which deposited cells form a cell surface;
   an image sensor having a lens and capturing images through the lens;
   an image data processor for processing the images to determine cell growth/migration; and
   an actuator adapted to, in response to a control signal at least partially determined by output of the image data processor, incrementally vary distance between the lens and the cell surface such that the images correspond to varying imaging depths.

2. Automated cell growth/migration detection system of claim 1, the actuator being adapted to vary distance at least once so that at least two images of the cell surface may be captured by the image sensor, each one of the two images corresponding to a different imaging depth.

3. Automated cell growth/migration detection system of claim 1, further comprising a frame coupled with one or all of the image sensor, lens and container, wherein at least one of (a) the actuator is adapted to translate the image sensor, relative to the frame, to vary the distance, (b) the actuator is adapted to translate the container, relative to the frame, to vary the distance, and (c) the actuator is adapted to translate the lens, relative to the frame, to vary the distance and vary separation between the lens and the image sensor.

4. Automated cell growth/migration detection system of claim 1, the image data processor adapted to store a first imaging cycle including first and second images of the cell surface obtained by the image sensor, the first and second images corresponding to first and second imaging depths of the varying imaging depths, respectively.

5. Automated cell growth/migration detection system of claim 4, the image processor further adapted to store, after the first imaging cycle, a second imaging cycle including third and fourth images of the cell surface obtained by the image sensor, the third and fourth images corresponding to third and fourth imaging depths of the varying image depths, respectively.

6. Automated cell growth/migration detection system of claim 5, the image processor further adapted to store at least one additional image of the cell surface, the additional image being obtained by the image sensor and corresponding respectively to at least one additional imaging depth of the varying imaging depths; the first imaging cycle further including the at least one additional image.

7. Automated cell growth/migration detection system of claim 5, the third and fourth imaging depths being the same as the first and second imaging depths, respectively.

8. Automated cell growth/migration detection system of claim 6, the image processor further adapted to store at least one further additional image of the cell surface obtained by the imaging sensor and corresponding respectively to at least one further imaging depth of the varying imaging depths; the second imaging cycle further including the at least one further additional image.

9. Automated cell growth/migration detection system of claim 5, the image processor further adapted to store at least one additional image of the cell surface, the additional image being obtained by the image sensor and corresponding respectively to at least one additional imaging depth of the varying imaging depths; the second imaging cycle further including the at least one additional image.

10. Automated cell growth/migration detection system of claim 8, each of the at least one further additional imaging depths being the same as the at least one additional imaging depth, respectively.

11. Automated cell growth/migration detection system of claim 10, the image sensor and the actuator are adapted to create further imaging cycles.

12. Automated cell growth/migration detection system of claim 11, wherein the image data processor determines a clearest-looking image for each imaging cycle.

13. Automated cell growth/migration detection system of claim 1, a first set of images corresponding to a first imaging cycle and a second set of images corresponding to a subsequent second imaging cycle, the first imaging cycle corresponding to a first sequence of imaging depths of the varying imaging depths, the second imaging cycle corresponding to a second sequence of imaging depths, the second sequence of imaging depths being the same as the first sequence of imaging depths, the image data processor adapted to:
process images from the first imaging cycle to isolate a first clearest-looking image corresponding to a first imaging depth of the first sequence of imaging depths,
process images from the second imaging cycle to isolate a second clearest-looking image corresponding to a second imaging depth, of the second sequence of imaging depths, wherein difference between the first and second imaging depths determines the cell growth/migration.

14. Automated cell growth/migration detection system of claim 1, wherein sequential sets of images of the cell surface correspond to sequential imaging cycles through incremental imaging depths over a total distance to form a two-dimensional image matrix processable to determine cell growth/migration.

15. Automated cell growth/migration detection system of claim 14, the image processor, or a computer connected with the image processor, adapted to algorithmically process the two-dimensional image matrix to determine the cell growth/migration.

16. Automated cell growth/migration detection system of claim 15, algorithmically processing comprising utilizing cell object boundaries in the two-dimensional image matrix.

17. Automated cell growth/migration detection system of claim 1, the control signal being generated by the image data processor.

18. Automated cell growth/migration detection system of claim 17, the image data processor being adapted to control the actuator such that, at the distance, the image sensor focuses on the cell surface.

19. Automated cell growth/migration detection system of claim 1, wherein the actuator sets the distance by (a) moving the image sensor along a frame, (b) moving the container along the frame, and/or (c) moving the lens along the frame.

20. Automated cell growth/migration detection method, comprising:
capturing a first series of images of a cell surface within a first imaging cycle corresponding to a sequence of imaging depths between the cell surface and an image sensor;
capturing an additional series of images of the cell surface within each of at least one additional imaging cycle and corresponding to the same sequence of imaging depths between the cell surface and an image sensor;
processing each series of images for each imaging cycle to determine a clearest-looking image; and
from the clearest-looking image of each imaging cycle, determining cell growth/migration.

21. Automated cell growth/migration detection method of claim 20, the cell surface being formed of deposited cells within a cell growth/migration matrix/medium held by a container, wherein the steps of capturing comprise varying the imaging depths by (a) moving the image sensor, (b) moving the container, and/or (b) by moving a lens of the image sensor.

* * * * *